United States Patent

[11] 4,051,067
[45] Sept. 27, 1977

Wilder

[54] STABILIZATION OF UNSATURATED CARBOXYLIC ACID ESTERS WITH MIXTURES OF POLYALKYLENEAMINES AND ARYLENEDIAMINES

[75] Inventor: Gene Ray Wilder, Medina, Ohio

[73] Assignee: Monsanto Company, St. Louis, Mo.

[21] Appl. No.: 644,613

[22] Filed: Dec. 29, 1975

Related U.S. Application Data

[62] Division of Ser. No. 436,438, Jan. 25, 1974, abandoned.

[51] Int. Cl.$^2$ .............................................. C09K 15/16
[52] U.S. Cl. .................................. 252/401; 260/239 B
[58] Field of Search ............... 260/486 R, 864, 239 B; 252/401

[56] References Cited

U.S. PATENT DOCUMENTS

| | | | |
|---|---|---|---|
| 2,266,576 | 12/1941 | Tuley et al. | 252/401 X |
| 2,318,211 | 5/1943 | Foord | 252/401 X |
| 2,796,336 | 6/1957 | Oldenburg | 252/401 X |
| 2,888,505 | 5/1959 | Broeck | 260/815 |
| 3,000,852 | 9/1961 | Merz | 252/401 X |
| 3,424,713 | 1/1969 | Oberster et al. | 252/401 X |
| 3,432,460 | 3/1969 | Spacht | 252/401 X |
| 3,480,617 | 11/1969 | Farhat | 260/239 B |
| 3,507,826 | 4/1970 | Lal et al. | 252/401 X |
| 3,855,281 | 12/1974 | Sullivan et al. | 260/486 R |
| 3,876,686 | 4/1975 | Sato | 260/486 R |
| 3,896,162 | 7/1975 | Mullins | 260/486 R |

OTHER PUBLICATIONS

*Condensed Chemical Dictionary*, (8th Ed.), New York: Van Nostrand Reinhold Co., 1971, 469.

*Primary Examiner* — Richard E. Schafer
*Assistant Examiner* — E. Suzanne Parr

[57] ABSTRACT

A method of inhibiting polymerization of unsaturated carboxylic acid esters and improved unsaturated carboxylic acid ester compositions are described. The method comprises, and the compositions are prepared by, incorporating into the ester composition a combination comprising polyalkyleneamine and arylenediamine of the formula

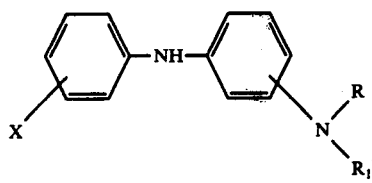

in which X is hydrogen, chloro, trichloromethyl, trifluoromethyl, nitro, lower alkyl, lower alkoxy or phenoxy, R is hydrogen or alkyl, and $R_1$ is alkyl or phenyl or R and $R_1$ together with the nitrogen atom is a heterocycle selected from the group consisting of pyrrolidinyl, 2,5-dimethyl pyrrolidinyl, piperidino and hexahydro-1H-azepin-1-yl.

14 Claims, No Drawings

STABILIZATION OF UNSATURATED CARBOXYLIC ACID ESTERS WITH MIXTURES OF POLYALKYLENEAMINES AND ARYLENEDIAMINES

This is a division of application Ser. No. 436,438 now abandoned, filed Jan. 25, 1974.

BACKGROUND OF THE INVENTION

This invention relates to methods of inhibiting polymerization of unsaturated monomers, more particularly it relates to methods of inhibiting polymerization of unsaturated carboxylic acid esters and to improved unsaturated carboxylic acid ester compositions. Processes concerning the preparation and the stabilization of unsaturated carboxylic esters are found in Patent Office Class 260, subclass 486.

Substantial quantities of unsaturated carboxylic acid esters, for example methyl methacrylate, are manufactured for use as intermediates in the production of polymers and copolymers. During manufacture, transportation and storage of these esters, it is essential that polymerization of these monomers is avoided. If premature polymerization occurs during manufacture, the polymer fouls or completely plugs production equipment and transfer lines which fouling leads to expensive dismantling and cleaning of production facilities. The problem is particularly acute during the distillation step which step is required to isolate the desired ester monomer. If premature polymerization occurs during transportation or storage, recovery of the polymer from the storage vessel is extremely difficult. Of course, any time that premature polymerization occurs, the yield of the desire monomer is reduced. It is common practice to add stabilizers to unsaturated esters to assure inhibition of polymerization. Preferred polymerization inhibitors not only prevent premature polymerization, they do not unduly interfere with the desired polymerization reaction or affect the polymer properties in any way. In polymer production, the effect of polymerization inhibitors is generally reduced by addition of polymerization initiators. Known polymerization inhibitors include phenols (hydroquinone being commonly used) and aliphatic and aromatic amines, for example, phenylenediamines. This invention concerns the stabilization of unsaturated carboxylic acid esters with mixtures of polyalkyleneamines and arylenediamines.

SUMMARY OF THE INVENTION

We have discovered that mixtures of polyalkyleneamines and certain N-aryl-o or p-phenylenediamines exhibit synergistic activity in respect to inhibiting the polymerization of unsaturated carboxylic acid esters. The inhibitor mixtures of this invention impart greater stability to unsaturated carboxylic acid esters than individual components alone. The unsaturated carboxylic acid ester compositions are stabilized by incorporating, by simple addition, the inhibitor mixture into the ester composition. Normally, the inhibitor mixture is added to the reactor after the ester is prepared but prior to distilling the reaction product to isolate the unsaturated ester from by-products and reaction media. Generally, additional quantities of the inhibitor mixture are added to the ester fraction recovered after distillation to inhibit polymerization during storage.

The inhibitor effect is concentration dependent, i.e., the more inhibitor mixture added, the longer the time period before the onset of polymerization. The inhibitor mixtures of this invention are particularly potent. Quantities of one part per million by weight or less based upon the weight of ester are sufficient to inhibit polymerization. Normally, 5–50 parts per million are recommended for most applications with amounts of 50–200 parts per million being used sometimes and 200–5000 parts per million being used where more severe conditions are encountered which require greater inhibition. Although even larger quantites are effective, higher dosages are usually unnecessary and are avoided for reason of economy. The amount required for any desired induction time may be readily determined by the methods hereinafter described. Enhanced stabilization of unsaturated ester is observed when the amount of the polyalkyleneamine is 10–90 parts by weight per 100 parts by weight inhibitor mixture. It being understood that the remainder of the inhibitor mixture is arylenediamine. Generally, the proportion of polyalkyleneamine of the inhibitor mixture is from 20–80 parts by weight per 100 parts by weight mixture, with amounts of 40–60 parts by weight per 100 parts by weight mixture being preferred. Often, equal amounts of polyalkyleneamine and arylenediamine are used.

The arylenediamine component of the inhibitor mixtures of this invention is characterized by the formula

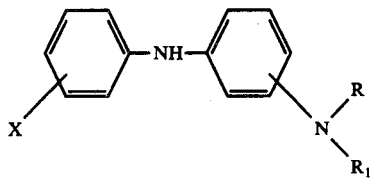

in which X is hydrogen, chloro, trichloromethyl, trifluoromethyl, nitro, lower alkyl, lower alkoxy or phenoxy, R is hydrogen or alkyl, $R_1$ is alkyl or phenyl or R and $R_1$ together with the nitrogen atom is a heterocyclic radical selected from the group consisting of pyrrolidinyl, 2,5-dimethyl pyrrolidinyl, piperidino and hexahydro-1H-azepin-1-yl. A preferred class of arylenediamines which exhibit especially potent inhibitor activity in combination with polyalkyleneamines comprise N-phenyl-p-phenylenediamines in which X is hydrogen, R is hydrogen or lower alkyl, $R_1$ is lower alkyl or R and $R_1$ together with the nitrogen is a heterocyclic radical.

Branched and unbranched primary, secondary and tertiary alkyl radicals of 1–10 carbon atoms are satisfactory. "Alkyl" means the radical derived from removal of one hydrogen atom from alkane. Illustrative examples of satisfactory alkyl radicals are methyl, ethyl, propyl, n-butyl, isobutyl, sec-butyl, tert-butyl, hexyl, 1,3-dimethylbutyl, heptyl, 1,4-dimethylpentyl, 2-ethylhexyl, octyl and tert-octyl (1,1,3,3-tetramethylbutyl). The term "lower alkyl" means alkyl radicals of 1–5 carbon atoms which radicals are a preferred subgroup of the invention.

The polyalkyleneamine component of the inhibitor mixture of the invention is; and the term polyalkyleneamine, as used herein and in the claims, means, in the generic sense, the class of amines characterized by acyclic and cyclic aliphatic compounds having amino groups attached through alkylene and mixtures thereof. Straight chain polyalkyleneamines containing 3–7 nitrogen atoms are preferred. The alkylene radicals may be straight or branched chains and may be the same or different in any polyalkyleneamine. Alkylene radicals of 1-10 carbon atoms are satisfactory with alkylene of 2-5 carbon atoms being preferred, and dimethylene being more preferred. Important subclasses of polyalkyleneamines are disclosed in U.S. Pat. No. 3,244,666 and U.S. Pat. No. 3,748,221, the disclosures of which are incorporated herein by reference.

Examples of suitable polyalkyleneamines are: diethylenetriamine, triethylenetetramine, tetraethylenepentamine, pebntaethylenehexamine, imino-bis propylamine, pentamethylenehexamine, diethyldiethylenetriamine, dipropylenetriamine, tripropylenetetramine, 4-(2-aminoethyl)diethylenetriamine, 4-(2-aminoethyl)triethylenetetramine, triethyltriethylenetetramine, 4-(2-aminoethyl)tetraethylenepentamine, 4,7-bis(2-aminoethyl)triethylenetetramine, diaminopropyltetramethylenediamine (spermine), 5,5'-diamino,2,2'bis-(aminomethyl)-dipentylamine, 3,3'-bis[(3-aminopropyl)amino]dipropylamine, hexaethyleneheptamine, and 2,5,8,11,14 pentamethylpentaethylenehexamine.

The term "unsaturated carboxylic acid ester" is used in the generic sense and means aliphatic esters of unsaturated mono-, di-, and tricarboxylic acids. Lower alkyl esters of ethylenically unsaturated monocarboxylic acids are preferred. The size of the carboxylic acid or ester moiety is immaterial. Polymerization of esters of unsaturated carboxylic acids of 30 carbon atoms or more are inhibited with the inhibitor mixtures of this invention. Illustrative examples of compounds stabilized with the inhibitor mixtures of this invention are the methyl, ethyl, butyl, and 2-ethylhexyl esters of the following acids: acrylic, methacrylic, angelic, crotonic, isocrotonic, propynoic, sorbic, oleic, elaidic, linoleic, α-eleostearic, β-eleostearic, α-linolenic and erucic. Other examples are the dimethyl, diethyl, dibutyl, and di(2-ethylhexyl) esters of maleic acid, fumaric acid, itaconic acid and acetylenedicarboxylic acid, and trialkyl esters of aconitic-(1,2,3-propenetricarboxylic acid). A preferred subgroup of unsaturated carboxylic acid esters are acrylate esters derived from acrylic and methyacrylic acids. These esters are characterized by the formula $CH_2=C(R_2)C(O)OR_3$ in which $R_2$ is hydrogen or methyl and $R_3$ is alkyl of 1-8 carbon atoms. Lower alkyl esters are preferred.

Examples of satisfactory N,N-dialkyl-N'-phenyl-phenylenediamines are:

N,N-dimethyl-N'-phenyl-p-phenylenediamine
N,N-diethyl-N'-phenyl-p-phenylenediamine
N,N-dipropyl-N'-phenyl-p-phenylenediamine
N,N-di-n-butyl-N'-phenyl-p-phenylenediamine N,N-di-sec-butyl-N'-phenyl-p-phenylenediamine
N,N-di-n-pentyl-N'-phenyl-p-phenylenediamine
N,N-di-n-hexyl-N'-phenyl-p-phenylenediamine
N,N-di-n-octyl-N'-phenyl-p-phenylenediamine
N-methyl-N-ethyl-N'-phenyl-p-phenylenediamine
N-methyl-N-propyl-N'-pheenyl-p-phenylenediamine
N-methyl-N-isopropyl-N'-phenyl-p-phenylenediamine
N-methyl-N-n-butyl-N'-phenyl-p-phenylenediamine
N-methyl-N-sec-butyl-N'-phenyl-p-phenylenediamine
N-methyl-N-isobutyl-N'-phenyl-p-phenylenediamine
N-methyl-N-tert-butyl-N'-phenyl-p-phenylenediamine
N-methyl-N-n-pentyl-N'-phenyl-p-phenylenediamine
N-methyl-N-hexyl-N'-phenyl-p-phenylenediamine
N-methyl-N-octyl-N'-phenyl-p-phenylenediamine
N-ethyl-N-propyl-N'-phenyl-p-phenylenediamine
N-ethyl-N-isopropyl-N'-phenyl-p-phenylenediamine
N-ethyl-N-n-butyl-N'-phenyl-p-phenylenediamine
N-ethyl-N-n-pentyl-N'-phenyl-p-phenylenediamine
N-ethyl-N-octyl-N'-phenyl-p-phenylenediamine
N-propyl-N-n-butyl-N'-phenyl-p-phenylenediamine
N-propyl-N-sec-butyl-N'-phenyl-p-phenylenediamine
and the corresponding ortho-phenylenediamines.

Examples of satisfactory N,N-dialkyl-N'-substituted-phenyl phenylenediamines are:

N,N-dimethyl-N'-(p-tolyl)-p-phenylenediamine
N,N-dimethyl-N'-(4-methoxyphenyl)-p-phenylenediamine
N,N-dimethyl-N'-(4-ethoxyphenyl)-p-phenylenediamine
N,N-dimethyl-N'-(4-nitrophenyl)-p-phenylenediamine
N,N-dimethyl-N'-(p-tolyl)-o-phenylenediamine
N,N-dimethyl-N'-(4-methoxyphenyl)-o-phenylenediamine
N,N-dimethyl-N'-(4-ethoxyphenyl)-o-phenylenediamine
N,N-diethyl-N'-(p-tolyl)-p-phenylenediamine
N,N-diethyl-N'-(4-methoxyphenyl)-p-phenylenediamine
N,N-diethyl-N'-(4-ethoxyphenyl)-p-phenylenediamine
N,N-diethyl-N'-(4-nitrophenyl)-p-phenylenediamine
N,N-dipropyl-N'-(p-tolyl)-p-phenylenediamine.

Illustrative examples of satisfactory N-alkyl-N'-phenyl-phenylenediamines are:

N-methyl-N'-phenyl-p-phenylenediamine
N-ethyl-N'-phenyl-p-phenylenediamine
N-propyl-N'-phenyl-p-phenylenediamine
N-isopropyl-N'-phenyl-p-phenylenediamine
N-butyl-N'-phenyl-p-phenylenediamine
N-isobutyl-N'-phenyl-p-phenylenediamine
N-sec.butyl-N'-phenyl-p-phenylenediamine
N-n-pentyl-N'-phenyl-p-phenylenediamine
N-n-hexyl-N'-phenyl-p-phenylenediamine
N-(1-methylhexyl)-N'-phenyl-p-phenylenediamine
N-(1,3-dimethylbutyl)-N'-phenyl-p-phenylenediamine
N-(1,4-dimethylpentyl)-N'-phenyl-p-phenylenediamine
N-n-octyl-N'-phenyl-p-phenylenediamine
N-(2-ethylhexyl)-N'-phenyl-p-phenylenediamine
N-(1-ethyl-3-methylpentyl)-N'-phenyl-p-phenylenediamine
N-tert-butyl-N'-phenyl-p-phenylenediamine
N-tert-amyl-N'-phenyl-p-phenylenediamine
N-tert-octyl-N'-phenyl-p-phenylenediamine.

Satisfactory heterocyclicamino-N-phenyl-phenylenediamines are N-(4-anilinophenyl)pyrrolidine, N-(4-anilinophenyl)-2,5-dimethyl-pyrrolidine, 1-(4-anilinophenyl)piperidine and 1-(4-anilinophenyl)hexahydro-1H-azepine.

The inhibitor mixtures of this invention extend the induction period prior to the onset of polymerization of unsaturated carboxylic acid ester monomer. The "onset time", the time from the beginning of the test until polymerization begins, may be conveniently determined either by measuring the temperature of a sample to detect the liberation of heat which takes place when polymerization begins or by measuring the change in volume of a sample to detect the volume reduction which takes place as polymerization proceeds. Either method is applicable to uncatalyzed samples or samples to which polymerization initiator is added. The exothermic method is described by Bockstahler, et al., *Ind &*

Eng. Chem., 50 (10), 1581. The dilatometric method is described by Caldwell and Ihrig, J. Am. Chem. Soc., 84, 2886.

The inhibitors of this invention are evaluated by the exothermic method essentially as described by Bockstahler, et al., supra. The time required for a test monomer to begin to polymerize is determined at elevated temperature. The test is based on the principle that polymerization is exothermic so that initiation is detected by observing temperature change between a test sample and a stable reference sample maintained in the same environment. The procedure comprises placing a test tube (adapted to accommodate a thermocouple) containing a measured amount of monomer in a constant temperature bath (maintained within ±0.25° C). A similar test tube containing silicone oil is used as a reference sample. A differential thermocouple continuously measures the difference in the temperature $\Delta T$ between the test and reference samples. All samples are measured in the dark to eliminate any effects due to light. The thermocouple output is recorded on a strip recorder thereby providing a record of $\Delta T$ versus time. When polymerization occurs a sharp deflection in $\Delta T$ is observed from which the onset time is determined.

DESCRIPTION OF PREFERRED EMBODIMENTS

Ethylmethacrylate is the test monomer used to illustrate the effect of the inhibitor mixtures of the invention. A supply of ethylmethacrylate containing hydroquinone inhibitors is repeatedly washed with 0.5 N sodium hydroxide solution and finally with water to remove all hydroquinone inhibitor from the material. Fifty grams of the unstabilized ethylmethacrylate is added to an above described test tube. A solution of inhibitor mixture is prepared by adding a carefully weighed quantity of inhibitor mixture to 10 ml of unstabilized ethylmethacrylate. The appropriate volume of inhibitor mixture solution is then added to the test sample with a micropipette to give the desired concentration. The test is placed in a constant temperature bath at 85° C and the onset time is determined as previously described. The onset time is recorded in hours. When the test is repeated, the average onset time is reported.

Improved acrylate compositions containing inhibitor mixtures of the invention comprising tetraethylenepentamine, triethylenetetramine, and Polyamine H are illustrated in Tables I, II and III respectively. Compositions comprising acrylate monomer and polyalkyleneamine and compositions comprising acrylate monomer and arylenediamine are included as controls. Compositions comprising acrylate monomer and mixtures of polyalkyleneamine and arylenediamine illustrate the invention. The data indicate that the acrylate compositions containing mixtures of polyalkyleneamine and arylenediamine exhibit substantially improved onset times.

TABLE I
ACRYLATE COMPOSITIONS COMPRISING 50/50 MIXTURES OF TETRAETHYLENEPENTAMINE/ARYLENEDIAMINES

| TETRA-ETHYLENE-PENTAMINE, ppm | ARYLENEDIAMINE | ppm | ONSET TIME, hrs |
|---|---|---|---|
| 5 | — | — | 16 |
| — | N,N'-(diphenyl)-p-phenylenediamine | 5 | 51 |
| 2.5 | N,N'-(diphenyl)-p-phenylenediamine | 2.5 | 110 |
| — | N-Tert-amyl-N'-phenyl-p-phenylenediamine | 5 | 119 |
| 2.5 | N-Tert-amyl-N'-phenyl-p-phenylenediamine | 2.5 | 178 |
| — | N,N-dimethyl-N'-phenyl-p-phenylenediamine | 2.5 | 83 |
| — | N,N-dimethyl-N'-phenyl-p-phenylenediamine | 5 | 137 |
| 2.5 | N,N-dimethyl-N'-phenyl-p-phenylenediamine | 2.5 | 160 |
| — | 1-(4-anilinophenyl)hexahydro-1H-azepine | 5 | 113 |
| 2.5 | 1-(4-anilinophenyl)hexahydro-1H-azepine | 2.5 | 226 |
| — | N,N-(diethyl)-N'-(phenyl)-p-phenylenediamine | 5 | 118 |
| 2.5 | N,N-(diethyl)-N'-(phenyl)-p-phenylenediamine | 2.5 | 172 |
| — | N-(1,3-dimethylbutyl)-N'-(phenyl)-p-phenylenediamine | 2.5 | 53 |
| — | N-(1,3-dimethylbutyl)-N'-(phenyl)-p-phenylenediamine | 5 | 84 |
| 2.5 | N-(1,3-dimethylbutyl)-N'-(phenyl)-p-phenylenediamine | 2.5 | 76 |

TABLE II
ACRYLATE COMPOSITIONS COMPRISING 50/50 MIXTURES OF TRIETHYLENETETRAMINE/ARYLENEDIAMINES

| TRIETHYLENE-TETRAMINE, ppm | ARYLENEDIAMINE | ppm | ONSET TIME, hrs. |
|---|---|---|---|
| 5 | — | — | 17 |
| — | N,N-(dimethyl)-N'-(4-methoxyphenyl)-p-phenylenediamine | 5 | 133 |
| 2.5 | N,N-(dimethyl)-N'-(4-methoxyphenyl)-p-phenylenediamine | 2.5 | 167 |
| — | N,N-(diisobutyl)-N'-phenyl-p-phenylenediamine | 2.5 | 52 |
| — | N,N-(diisobutyl)-N'-phenyl-p-phenylenediamine | 5 | 88 |
| 2.5 | N,N-(diisobutyl)-N'-phenyl-p-phenylenediamine | 2.5 | 89 |

TABLE III
ACRYLATE COMPOSITIONS COMPRISING 50/50 MIXTURES OF POLYAMINE H/ARYLENEDIAMINES

| POLYAMINE H*, ppm | ARYLENEDIAMINE | ppm | ONSET TIME, hrs. |
|---|---|---|---|
| 5 | — | — | 16 |
| — | N-(Tert-butyl)-N'-phenyl-p-phenylenediamine | 5 | 110 |
| 2.5 | N-(Tert-butyl)-N'-phenyl-p-phenylenediamine | 2.5 | 153 |
| — | N,N-(diethyl)-N'-(phenyl)-p-phenylenediamine | 2.5 | 93 |
| — | N,N-(diethyl)-N'-(phenyl)-p-phenylenediamine | 5 | 118 |
| 2.5 | N,N-(diethyl)-N'-(phenyl)-p-phenylenediamine | 2.5 | 171 |
| — | N-(alkyl)-N'-(phenyl)-p-phenylenediamine mixture** | 5 | 57 |
| 2.5 | N-(alkyl)-N'-(phenyl)-p-phenylenediamine mixture** | 2.5 | 86 |

*Polyamine H is a product of Union Carbide Corporation and is believed to be a mixture of polyethyleneamines.
**A mixture comprising 2 parts N-(1,4-dimethylpentyl)-N'-(phenyl)-p-phenylenediamine and 1 part N-(1,3-dimethyl-butyl)-N'-(phenyl)-p-phenylenediamine.

The effect of varying the ratio of polyalkyleneamine and arylenediamine is illustrated in Table IV. The data show that maxium inhibition of polymerization (longest onset times) are achieved when the ratio of polyalkyleneamine and arylenediamine is about 1/1.

TABLE IV

ACRYLATE COMPOSITIONS COMPRISING MIXTURES OF TETRAETHYLENEPENTAMINE AND N(ALKYL)-N'-(PHENYL)-P-PHENYLENEDIAMINE MIXTURE

| TETRA-ETHYLENE-PENTAMINE, ppm | N(Alkyl)-N-'(phenyl)-p-phenylenediamine mixture**, ppm | ONSET TIME, hrs. |
|---|---|---|
| 5 | — | 16 |
| 4 | 1 | 46 |
| 3 | 2 | 74 |
| 2.5 | 2.5 | 91 |
| 2 | 3 | 91 |
| 1 | 4 | 72 |
| — | 5 | 57 |

**A mixture comprising 2 parts N-(1,4-dimethylpentyl)-N(phenyl)-p-phenylenediamine and 1 part N-(1,3-dimethylbutyl)-N(phenyl)-p-phenylenediamine.

Although the invention has been illustrated by typical examples, it is not limited thereto. Changes and modifications of the examples of the invention herein chosen for purposes of disclosure can be made which do not constitute departure from the spirit and scope of the invention.

I claim:

1. An inhibitor composition comprising polyalkyleneamine which is an acyclic aliphatic compound having amino groups attached through alkylene of 1–10 carbon atoms and arylenediamine of the formula

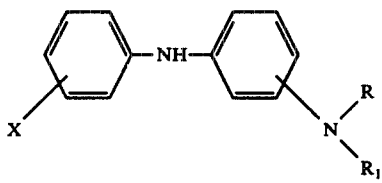

in which X is hydrogen, chloro, trichloromethyl, trifluoromethyl, nitro, lower alkyl, lower alkoxy, or phenoxy, R is hydrogen or alkyl, $R_1$ is alkyl or phenyl, or R and $R_1$ together with the nitrogen atom is a heterocyclic radical selected from the group consisting of pyrrolidinyl, 2,5-dimethylpyrrolidinyl, piperidino and hexahydro-1H-azepin-1-yl in which the polyalkyleneamine is 10–90 parts by weight and the arylenediamine is 10–90 parts by weight per 100 parts by weight of the inhibitor composition.

2. The composition of claim 1 which comprises 20–80 parts by weight polyalkyleneamine and 20–80 parts by weight arylenediamine per 100 parts by weight of the composition.

3. The composition of claim 2 in which the arylenediamine is a p-phenylenediamine and X is hydrogen.

4. The composition of claim 3 in which the polyalkyleneamine is a polyethyleneamine of 3–7 nitrogen atoms.

5. The composition of claim 4 in which the polyethyleneamine is tetraethylenepentamine.

6. The composition of claim 4 in which R and $R_1$ are lower alkyl.

7. The composition of claim 6 in which R and $R_1$ are methyl.

8. The composition of claim 4 in which R is hydrogen and $R_1$ is phenyl.

9. The composition of claim 4 in which R is hydrogen and $R_1$ is lower alkyl.

10. The composition of claim 9 in which $R_1$ is tertamyl.

11. The composition of claim 4 in which

is heterocyclic radical.

12. The composition of claim 11 in which

is hexahydro-1H-azepin-1-yl.

13. The composition of claim 4 in which the arylenediamine is N-(1,3-dimethylbutyl)-N'-(phenyl)-p-phenylenediamine.

14. The composition of claim 4 in which the arylenediamine is a mixture comprising N-(1,4-dimethylpentyl)-N'-(phenyl)-p-phenylenediamine and N-(1,3-dimethylbutyl)-N'-(phenyl)-o-phenylenediamine.

* * * * *